US008660634B2

(12) United States Patent
Patz et al.

(10) Patent No.: US 8,660,634 B2
(45) Date of Patent: Feb. 25, 2014

(54) SYSTEM AND METHOD FOR IMPROVED LUNG FOURIER DECOMPOSITION MAGNETIC RESONANCE IMAGING

(75) Inventors: Samuel Patz, Chestnut Hill, MA (US); James P Butler, Brookline, MA (US)

(73) Assignee: The Brigham and Woman's Hospital, Boston, MA (US)

( * ) Notice: Subject to any disclaimer, the term of this patent is extended or adjusted under 35 U.S.C. 154(b) by 114 days.

(21) Appl. No.: 13/453,493

(22) Filed: Apr. 23, 2012

(65) Prior Publication Data

US 2013/0281830 A1 Oct. 24, 2013

(51) Int. Cl.
*A61B 5/055* (2006.01)

(52) U.S. Cl.
USPC ............................ 600/413; 600/407; 600/410

(58) Field of Classification Search
USPC .......................................... 600/407, 410, 413
See application file for complete search history.

(56) References Cited

U.S. PATENT DOCUMENTS

| 6,593,144 | B2 * | 7/2003 | Albert et al. | 436/173 |
| 7,006,860 | B2 * | 2/2006 | Menon | 600/422 |
| 7,174,200 | B2 * | 2/2007 | Salerno et al. | 600/420 |
| 7,357,917 | B2 * | 4/2008 | Driehuys | 424/9.3 |
| 7,805,176 | B2 * | 9/2010 | Ruppert et al. | 600/407 |
| 7,991,449 | B2 * | 8/2011 | Ehman et al. | 600/407 |

OTHER PUBLICATIONS

Bauman, et al., Non-Contrast-Enhanced Perfusion and Ventilation Assessment of the Human Lung by Means of Fourier Decomposition in Proton MRI, Magnetic Resonance in Medicine, 2009, 62(3):656-664.
Chefd'Hotel, et al., A Variational Approach to Multi-Modal Image Matching, IEEE Workshop on Variational and Level Set Methods in Computer Vision, Vancouver, 2001, pp. 21-28.
Deimling, True FISP Imaging of Lung Parenchyma at 0.2 Tesla, Proc. Intl. Soc. Mag. Reson. Med., 2000, 8:2202.
Deimling, et al., Time Resolved Lung Ventilation Imaging by Fourier Decomposition, Proc. Intl. Soc. Mag. Reson. Med., 2008, 16:2639.
Zapke, et al., Magnetic Resonance Lung Function—A Breakthrough for Lung Imaging and Functional Assessment? A Phantom Study and Clinical Trial, Respiratory Research, 2006, 7:106, 9 pages.

* cited by examiner

*Primary Examiner* — Peter Luong
(74) *Attorney, Agent, or Firm* — Quarles & Brady, LLP (57) ABSTRACT

A system and method for producing a more accurate ventilation image, as compared to existing lung Fourier decomposition methods, and an image of ventilation dependent blood volume are provided. A time series of images depicting a subject's lungs during free-breathing are acquired and co-registered to a reference image. From the registration process, geometric information indicative proton density changes due to inhalation and exhalation of gas is obtained. This geometric information is used to correct the proton density values in the time series of image frames. These corrected proton density values are Fourier transformed to produce a Fourier spectrum, from which a signal peak occurring at the breathing frequency is extracted and Fourier transformed to produce a more accurate ventilation image. This more accurate ventilation image can be subtracted from a breathing frequency image produced by conventional lung Fourier decomposition methods to produce a ventilation dependent blood volume image.

17 Claims, 4 Drawing Sheets

SYSTEM AND METHOD FOR IMPROVED LUNG FOURIER DECOMPOSITION MAGNETIC RESONANCE IMAGING

STATEMENT REGARDING FEDERALLY SPONSORED RESEARCH

This invention was made with government support under Grant No. HL100606 awarded by the National Institutes of Health. The government has certain rights in this invention.

BACKGROUND OF THE INVENTION

The field of the invention is systems and methods for magnetic resonance imaging ("MRI"). More particularly, the invention relates to systems and methods for improved lung Fourier decomposition MRI.

Pulmonary proton MRI has long faced challenges of low signal-to-noise ratio ("SNR") because a majority of the lung is gas with low proton density. A promising new approach to lung imaging with MRI acquires serial images during free tidal breathing. Each image from a different time point in the breathing cycle is registered to a reference image and the time series of each voxel is Fourier transformed. Peaks in the spectrum at the breathing and heart rate frequencies are used to identify the amplitude of regional proton density changes related to "ventilation" and "perfusion" respectively. This method is known as the lung Fourier decomposition method. In the spatial registration procedure, the position and size of each voxel is registered to a corresponding voxel in a reference image. The change in proton density at the breathing frequency is entirely attributed to the modulation of proton density due to changes in gas volume during ventilation. However, as lung volume changes due to inhalation or exhalation, proton density may be further changed due to a change in blood volume. For example, increasing lung volume may act to reduce proton density even further due to a decrease in blood volume secondary to the stretching of alveolar septa and compressive force on the capillary blood. Thus, conventional Fourier decomposition methods provide an inaccurate representation of proton density changes associated with ventilation.

In addition, conventional Fourier decomposition methods do not provide information about the ventilation dependent lung blood volume. The ability to obtain an image of this ventilation dependent blood volume via noninvasive means, such as MRI, has yet to be achieved. An image that depicts ventilation dependent blood volume has the potential to be a valuable noninvasive pulmonary function test that may have significant diagnostic value.

It would therefore be desirable to provide a system and a method that provides a decomposition of proton density changes observed at the breathing frequency that are due to true ventilation and to changes in blood volume that are caused by ventilation.

SUMMARY OF THE INVENTION

The present invention overcomes the aforementioned drawbacks by providing a method for producing an image indicative of ventilation in a subject using a magnetic resonance imaging ("MRI") system. A time series of images depicting a subject's lungs while the subject is breathing is acquired using the MRI system. Each image in the time series of images includes a plurality of voxels located within a field-of-view. Each image in the acquired time series of images is registered to a reference image. Geometric information indicative of proton density changes in each voxel in the field-of-view due to inhalation and exhalation is also obtained from the image registration. Proton density values in each voxel in the time series of images are corrected using the obtained geometric information. The corrected proton density values are indicative of changes in proton density due to changes in gas volume in the subject's lung. A Fourier spectrum is produced for each voxel in the field-of-view by Fourier transforming the corrected time series of images. Each Fourier spectrum includes a signal peak associated with a frequency of the subject's breathing rate. A signal peak in each voxel that is associated with a frequency of the subject's breathing rate is extracted from the produced Fourier spectra. An image indicative of ventilation in the subject is then produced using these extracted signal peaks.

This ventilation image is more accurate than those produced with conventional lung Fourier decomposition methods. A conventional Fourier decomposition method may be used to produce a breathing rate frequency image. By subtracting the more accurate ventilation image from this breathing rate frequency image, an image that depicts ventilation dependent blood volume may be produced.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

A system and method for producing images with a magnetic resonance imaging ("MRI") system that provide improvements to lung Fourier decomposition imaging are provided. A Fourier decomposition method is used to separate hydrogen proton magnetic resonance signal changes at both the breathing frequency and the heart rate frequency. The heart rate frequency associated changes are identified as "perfusion" as in current Fourier decomposition methods. The inventors have identified that the proton magnetic resonance signal changes at the breathing frequency are not an accurate representation of the actual ventilation-induced changes in proton density in the lung. Rather, these conventional breathing rate frequency images include proton density changes related to both the inhalation and exhalation of gases, and to proton density changes related to blood volume changes that occur during respiration.

Thus, the conventional Fourier decomposition method produces a breathing rate frequency image that is contaminated by the proton density changes associated with blood volume changes that occur during respiration. This error leads to a misinterpretation of the data and provides incorrect functional information about the lung. The inventors have identified that these two breathing rate frequency signal components are comparable in magnitude and, therefore, the signal contamination caused by blood volume changes is significant. In addition, the inventors have identified that the ventilation dependent blood volume ("VDBV") image may also be of considerable diagnostic value because it provides an independent measure of pulmonary function associated with the compliance of blood vessels in the lung.

The present invention provides a system and method capable of separating the two breathing rate signal components described above, thereby resulting in images that more accurately convey information about lung function when compared to those available with conventional Fourier decomposition methods. The present invention also provides new information in the form of a ventilation dependent blood volume image. With conventional Fourier decomposition methods, the amplitude of the Fourier spectrum at the breathing frequency and at the heart rate frequency are extracted. However, as discussed above, the breathing rate frequency image obtained with this conventional approach includes two components. The first component represents changes in lung density due only to the inhalation or exhalation of air, and the second component represents changes due to blood volume changes associated with expansion or contraction of the lung blood vessels while the patient is breathing. It is noted that the proton density time dependence associated with inhalation or exhalation of air is not necessarily in phase with proton density changes associated with changes in blood volume, and may be diagnostic of mismatches of ventilation and perfusion. The change in the size of each image voxel during respiration is obtained from the geometric registration of a time series of image frames acquired when the patient is breathing freely. The true ventilation image—that is, the change in proton density due solely to inhalation or exhalation of air—may be produced from this geometric information. Thus, the inventors have discovered that geometric information obtained from image registration is indicative of the proton density change due solely to the inhalation and exhalation of gas.

The image registration process is able to obtain geometric information that is indicative of proton density changes associated with inhalation and exhalation of gas because of the following reasons. In the lung, there are multiple bifurcating "bundles" that each contain an airway bronchus, an artery, and a vein. These bundles ramify in a tree-like manner throughout the lung. During breathing, the spacing between the bundles expands or contracts. In addition, the diameter of the blood vessels may also change size. The spatial registration algorithm operates on the change in spacing between bundles due to inhalation or exhalation of air, but will not be sensitive to a change in the diameter of the individual components of the bundle, such as the bronchi and blood vessels. Because the spatial registration algorithm only addresses the spacing between bundles, it is insensitive to blood volume effects and, therefore, is a better indicator of the change in proton density due to ventilation.

Because the breathing rate image obtained with conventional Fourier decomposition methods includes signal contributions from both sources, the true ventilation image can be subtracted from the conventional Fourier decomposition breathing rate image to obtain an image that depicts the ventilation dependent blood volume changes. This image provides previously unattainable diagnostic pulmonary functional information. It is noted that this effect can be increased with larger tidal volumes. At increasingly larger lung volumes in normal subjects, the magnitude of the change in blood volume also increases.

It is contemplated that the ventilation dependent blood volume image will be advantageous for diagnosing pulmonary disease associated with fibrosis. For example, it is contemplated that voxel intensity values in this image will be reduced in areas where fibrosis occurs because fibrotic alveolar septa are essentially incompressible. Thus, the blood volume component is small and this, together with the fact that stiff, incompressible vessels tend to preserve luminal volumes, implies that the proton density changes associated with blood volume changes will be correspondingly small. This clinical application is important because there are currently no ways to sensitively and noninvasively diagnose interstitial disease. Presently, x-ray computed tomography ("CT") is the most commonly used method to diagnose pulmonary fibrosis; however, this technique is not sensitive to early stages of the disease and requires the exposing the patient to ionizing radiation. Because patients with interstitial lung disease must be frequently followed—typically receiving at least one CT scan per year—an imaging method that routinely exposes them to ionizing radiation is problematic. An MRI method that is capable of detecting interstitial disease would be clinically very valuable.

Figure 1:
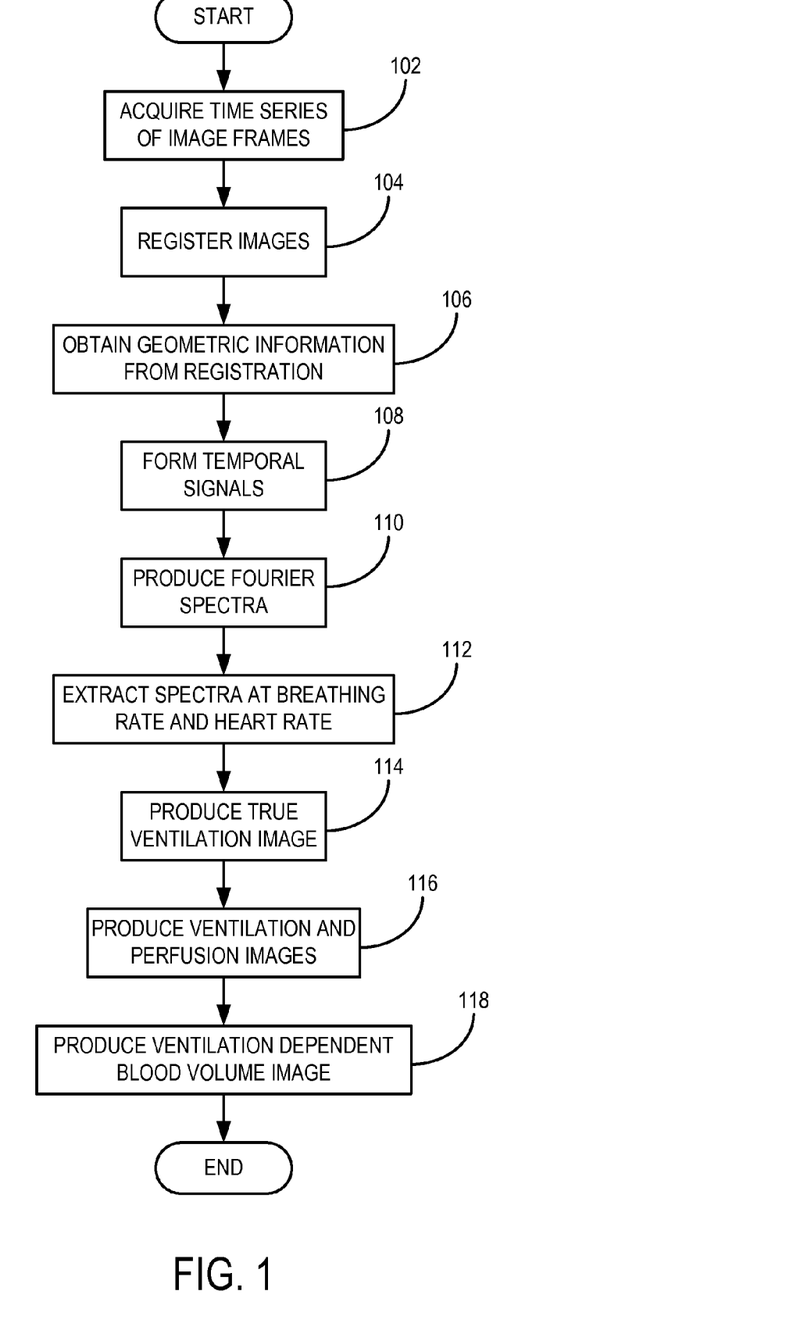
FIG. 1 is a flowchart setting forth the steps of an example of a method for producing a more accurate ventilation image and a ventilation dependent blood volume image from a time series of hydrogen proton magnetic resonance images.

Referring now to FIG. 1, a flowchart setting for an example of a method for producing a ventilation dependent blood volume image of a subject is illustrated. The method begins with the acquisition of a time series of image frames, as indicated at step 102. For example, k-space data is acquired from the subject using an MRI system, from which images of the subject can be reconstructed. The images in the time series are then co-registered, as indicated at step 104. For example, the images may be registered to a reference image, such as an image that is identified as representing the patient's lungs half way between inhalation and exhalation. As an example, a non-rigid transformation that tracks the displacement of each position within the lung may be used. As a part of the registration, information indicative of geometric changes in the size of voxels in the field-of-view depicted by the image frames is obtained, as indicated at step 106. This geometric information is representative of the changes in proton density due solely to true ventilation and, for this reason, is stored for subsequent processing to produce a true ventilation image. It is noted that when data is acquired from a single slice rather a full three-dimensional volume the geometric information obtained from the registration process will only account for volume changes in two of the three spatial dimensions. However, when the two-dimensional images are coronal images where the slice-selection direction is anterior-posterior ("AP"), lung motion in the AP direction is likely to be negligible.

Figure 2A:
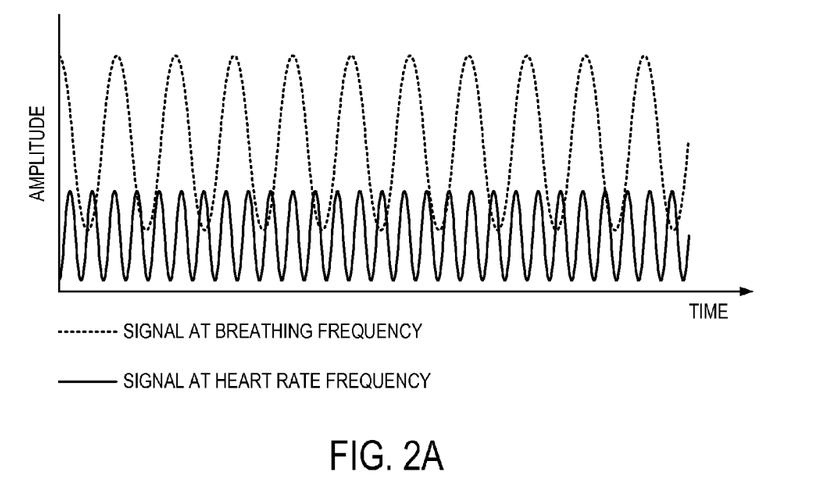
FIG. 2A is an example of a component of a temporal signal that is oscillating with a patient's breathing rate and a component of a temporal signal that is oscillating with the patient's heart rate.
Figure 2B:
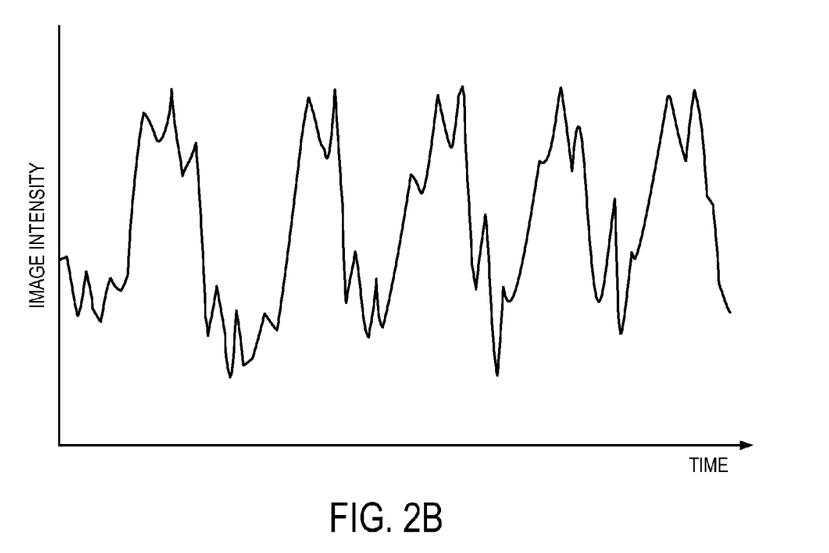
FIG. 2B is an example of a composite temporal signal derived from a time series of image frames, the composite temporal signal including a component oscillating with the patient's breathing rate and a component oscillating with the patient's heart rate.
Figure 3:
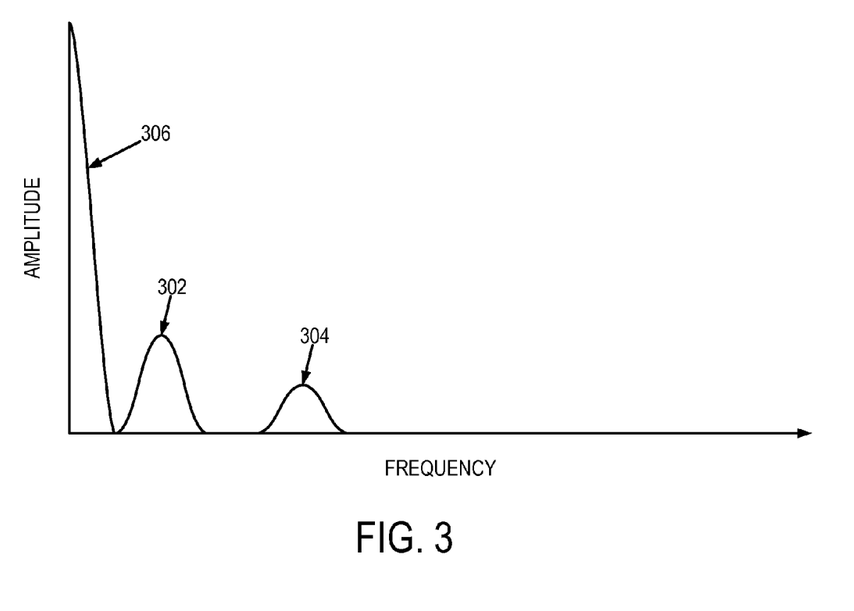
FIG. 3 is an example of a Fourier spectrum including a spectral peak at the patient's breathing rate frequency, a spectral peak at the patient's heart rate frequency, and a DC spectral peak.

For each spatially-registered voxel location in the image field-of-view, a temporal signal is formed, as indicated at step 108. Each temporal signal indicates the changes in image intensity values at the respective voxel location over the time course spanned by the time series of image frames. In general, these temporal signals include oscillations, such as sinusoidal oscillations, occurring at the patient's breathing rate frequency and at the patient's heart rate frequency. An example of the components of the temporal signals that oscillate at these frequencies is illustrated in FIG. 2A, whereas an example of a temporal signal that includes a superposition of these signal components is illustrated in FIG. 2B. These temporal signals are Fourier transformed to produce a Fourier spectrum for each voxel location, as indicated at step 110. These resulting Fourier spectra contain several peaks, some of which are related to proton density changes occurring at or near the frequency of the subject's heart rate, and some of which are related to proton density changes occurring at the frequency of the subject's breathing rate. An example of a Fourier spectrum that contains a spectral peak 302 at the breathing rate frequency and a spectral peak 304 at the heart rate frequency is illustrated in FIG. 3. The heart rate peak 304 is a higher frequency peak than the breathing rate peak 302 because respiration is a low-frequency movement relative to the beating heart. Note also that there is a strong DC frequency peak 306 in the Fourier spectrum. This peak is representative of the static structures at the voxel location.

Next, the Fourier spectral peaks at the breathing rate frequency and at the heart rate frequency are extracted to produce breathing rate spectra and heart rate spectra, as indicated at step 112. Having extracted these spectral components, images representative of ventilation, ventilation dependent blood volume, and perfusion can now be produced.

As discussed above, the conventional breathing rate frequency image represented by the extracted spectral peak occurring at the breathing rate frequency includes information pertaining to proton density changes occurring from both respiration and blood volume changes. The latter contribution contaminates the true ventilation signal; thus, the geometric information obtained from the image registration procedure is used to produce a true ventilation image, as indicated at step 114. To produce this true ventilation image, the geometric information obtained from the registration procedure is used to create a new set of spatially-registered images that depict proton density values in each voxel that are indicative of proton density changes due to gas volume changes in the subject's lungs. These spatially-registered images are Fourier transformed to produce a Fourier spectrum, from which a more accurate ventilation signal can be extracted as the signal peak occurring at the breathing frequency. Because this geometric information describes how the size of the voxels changed during the time course, the Fourier transform of the proton density values that have been corrected with this information will produce a spectral peak at the breathing rate frequency that results only from the proton density changes caused by the inhalation and exhalation of gas—that is, ventilation. This spectral peak can be extracted to obtain the true ventilation signal, $V_T(i)$, for the image voxel indexed by the index, i, which can be assigned an image intensity value to produce the true ventilation image. It is noted that the integral of the spectral peak, rather than just the peak value, can also be assigned to the image intensity values in the ventilation image. This true ventilation signal, $V_T(i)$, is preferably normalized by dividing the true ventilation signal by the total signal for the voxel, $S_0(i)$, $$\overline{V}_T(i) = \frac{V_T(i)}{S_0(i)}. \tag{1}$$

The normalized true ventilation signal is then the fraction of the tissue in the $i^{th}$ voxel whose proton density is changing at the breathing frequency relative to the tissue that is static.

As indicated at step 116, conventional breathing rate and perfusion images may be produced from the breathing rate frequency peak and heart rate frequency peak, respectively. For example, the extracted spectral information can be assigned to image intensity values to produce the respective images. As discussed above, the breathing rate image produced from this breathing rate frequency peak is not the true ventilation image; rather, it is a measure of the total change in tissue volume within a voxel due to two effects: the expansion of the lung due to inhalation of gas and the change in blood volume that is dependent on the level of ventilation. It is still useful, however, to produce the conventional Fourier decomposition breathing rate image because it can be used to generate an image of the ventilation dependent blood volume changes, as indicated at step 118. For example, the breathing rate frequency signal obtained by the traditional Fourier decomposition method, $V_{FD}(i)$, and the true ventilation signal, $V_T(i)$, computed above can be used to produce a ventilation dependent blood volume signal, $V_{BV}(i)$. Because this ventilation dependent blood volume signal is a fractional signal, the Fourier decomposition ventilation signal is preferably first normalized by the total signal at the voxel, $$\overline{V}_{FD}(i) = \frac{V_{FD}(i)}{S_0(i)}. \tag{2}$$

Then, the ventilation dependent blood volume signal can be calculated as follows:

$$\overline{V}_{BV}(i) = \overline{V}_{FD}(i) - \overline{V}_T(i) \tag{3}.$$

Figure 4:
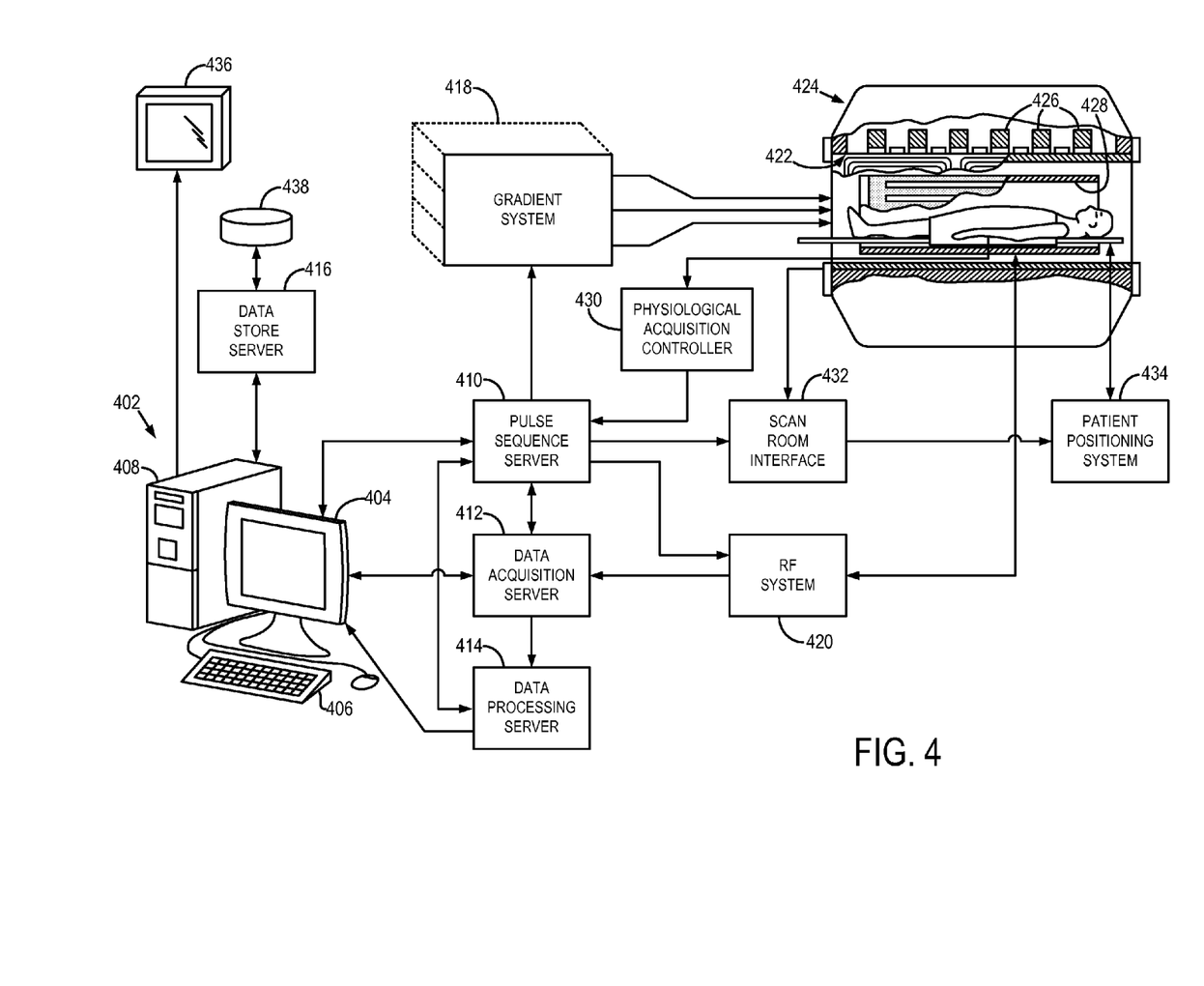
FIG. 4 is a block diagram of an example of a magnetic resonance imaging ("MRI") system.

Referring now to FIG. 4, an example of a magnetic resonance imaging ("MRI") system is illustrated. The MRI system includes a workstation 402 having a display 404 and a keyboard 406. The workstation 402 includes a processor 408, such as a commercially available programmable machine running a commercially available operating system. The workstation 402 provides the operator interface that enables scan prescriptions to be entered into the MRI system. The workstation 402 is coupled to four servers: a pulse sequence server 410; a data acquisition server 412; a data processing server 414, and a data store server 416. The workstation 402 and each server 410, 412, 414 and 416 are connected to communicate with each other.

The pulse sequence server 410 functions in response to instructions downloaded from the workstation 402 to operate a gradient system 418 and a radio frequency ("RF") system 420. Gradient waveforms necessary to perform the prescribed scan are produced and applied to the gradient system 418, which excites gradient coils in a gradient coil assembly 422 to produce the magnetic field gradients $G_x$, $G_y$, and $G_z$ used for position encoding MR signals. The gradient coil assembly 422 forms a part of a magnet assembly 424 that includes a polarizing magnet 426 and a whole-body RF coil 428.

RF excitation waveforms are applied to the RF coil 428, or a separate local coil (not shown in FIG. 4), by the RF system 420 to perform the prescribed magnetic resonance pulse sequence. Responsive MR signals detected by the RF coil 428, or a separate local coil (not shown in FIG. 4), are received by the RF system 420, amplified, demodulated, filtered, and digitized under direction of commands produced by the pulse sequence server 410. The RF system 420 includes an RF transmitter for producing a wide variety of RF pulses used in MR pulse sequences. The RF transmitter is responsive to the scan prescription and direction from the pulse sequence server 410 to produce RF pulses of the desired frequency, phase, and pulse amplitude waveform. The generated RF pulses may be applied to the whole body RF coil 428 or to one or more local coils or coil arrays (not shown in FIG. 4).

The RF system 420 also includes one or more RF receiver channels. Each RF receiver channel includes an RF amplifier that amplifies the MR signal received by the coil 428 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \quad (4);$$

and the phase of the received MR signal may also be determined:

$$\phi = \tan^{-1}\left(\frac{Q}{I}\right). \quad (5)$$

The pulse sequence server 410 also optionally receives patient data from a physiological acquisition controller 430. The physiological acquisition controller 430 receives signals from a number of different sensors connected to the patient, such as electrocardiograph ("ECG") signals from electrodes, or respiratory signals from a bellows or other respiratory monitoring device. Such signals are typically used by the pulse sequence server 410 to synchronize, or "gate," the performance of the scan with the subject's heart beat or respiration.

The pulse sequence server 410 also connects to a scan room interface circuit 432 that receives signals from various sensors associated with the condition of the patient and the magnet system. It is also through the scan room interface circuit 432 that a patient positioning system 434 receives commands to move the patient to desired positions during the scan.

The digitized MR signal samples produced by the RF system 420 are received by the data acquisition server 412. The data acquisition server 412 operates in response to instructions downloaded from the workstation 402 to receive the real-time MR data and provide buffer storage, such that no data is lost by data overrun. In some scans, the data acquisition server 412 does little more than pass the acquired MR data to the data processor server 414. However, in scans that require information derived from acquired MR data to control the further performance of the scan, the data acquisition server 412 is programmed to produce such information and convey it to the pulse sequence server 410. For example, during prescans, MR data is acquired and used to calibrate the pulse sequence performed by the pulse sequence server 410. Also, navigator signals may be acquired during a scan and used to adjust the operating parameters of the RF system 420 or the gradient system 418, or to control the view order in which k-space is sampled.

The data processing server 414 receives MR data from the data acquisition server 412 and processes it in accordance with instructions downloaded from the workstation 402. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 414 are conveyed back to the workstation 402 where they are stored. Real-time images are stored in a data base memory cache (not shown in FIG. 4), from which they may be output to operator display 412 or a display 436 that is located near the magnet assembly 424 for use by attending physicians. Batch mode images or selected real time images are stored in a host database on disc storage 438. When such images have been reconstructed and transferred to storage, the data processing server 414 notifies the data store server 416 on the workstation 402. The workstation 402 may be used by an operator to archive the images, produce films, or send the images via a network to other facilities.

Thus, a system and method for producing a true ventilation image from hydrogen proton magnetic resonance images have been provided, thereby providing an improvement over conventional lung Fourier decomposition imaging. The system and method are also capable of determining the proton density change associated with blood volume changes during ventilation, which can be used as an independent, noninvasive, and regional measure of interstitial fibrosis.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an image indicative of ventilation in a subject using a magnetic resonance imaging (MRI) system, the steps of the method comprising:
 a) acquiring a time series of images depicting a subject's lungs while the subject is breathing using the MRI system, each image in the time series of images having a plurality of voxels located within a field-of-view;
 b) registering each image in the time series of images acquired in step a) to a reference image;
 c) obtaining geometric information indicative of proton density changes in each voxel in the field-of-view due to inhalation and exhalation from the registration performed in step b);
 d) correcting proton density values in each voxel in the time series of images using the geometric information obtained in step c), the corrected proton density values being indicative of changes in proton density due to changes in gas volume in the subject's lung;
 e) producing a Fourier spectrum for each voxel in the field-of-view that includes a signal peak associated with a frequency of the subject's breathing rate by Fourier transforming the corrected time series of images corrected in step d);
 f) extracting the signal peak in each voxel that is associated with a frequency of the subject's breathing rate from the Fourier spectra produced in step e); and
 g) producing an image indicative of ventilation in the subject using the signal peaks extracted in step f).

2. The method as recited in claim 1 in which step g) includes assigning for each voxel in the image indicative of ventilation, a value of the signal peak extracted in step f) to an image intensity value in the image.

3. The method as recited in claim 2 in which the value of the signal peak is an integrated intensity over the signal peak.

4. The method as recited in claim 1 in which step g) includes normalizing the image intensity value at each voxel with respect to a total Fourier signal in the respective voxel.

5. The method as recited in claim 4 in which the total signal is calculated as a sum of Fourier components at a voxel location of the respective voxel.

6. The method as recited in claim 4 further comprising h) producing an image indicative of a ventilation dependent blood volume using the image indicative of ventilation produced in step g).

7. The method as recited in claim 6 in which the image indicative of ventilation dependent blood volume is produced in step h) by:

i) forming from the time series of images, a temporal signal at each voxel in the field-of-view;

ii) producing a Fourier spectrum at each voxel by Fourier transforming the respective temporal signal;

iii) extracting a signal peak in each voxel that is associated with a frequency of the subject's breathing rate from the Fourier spectra produced in step ii);

iv) producing an image indicative of both ventilation and ventilation dependent blood volume using the signal peaks extracted in step iii);

v) normalizing the image produced in step iv) with respect to a total Fourier signal for each respective voxel in the image; and vi) subtracting the image produced in step g) and the image produced in step h)v).

8. The method as recited in claim 6 further comprising determining a phase between a ventilation signal associated with the image produced in step g) and a ventilation dependent blood volume signal associated with the image produced in step h).

9. The method as recited in claim 1 in which step b) includes performing a non-rigid registration of each image in the time series of images with a reference image.

10. The method as recited in claim 1 in which the reference image to which image in the time series of images is registered in step b) is selected as an image from the time series of images that represents the subject's lungs mid way between inhalation and exhalation.

11. A magnetic resonance imaging (MRI) system, comprising:

a magnet system configured to generate a polarizing magnetic field about at least a portion of a subject arranged in the MRI system;

a plurality of gradient coils configured to establish at least one magnetic gradient field to the polarizing magnetic field;

a radio frequency (RF) system configured to apply an RF field to the subject and to receive magnetic resonance signals therefrom;

a computer system programmed to:

direct the MRI system to acquire a time series of images depicting a subject's lungs while the subject is breathing, each image in the time series of images having a plurality of voxels located within a field-of-view;

register each image in the time series of images to a reference image;

obtain geometric information indicative of proton density changes in each voxel in the field-of-view due to inhalation and exhalation from the registration;

correct proton density values in each voxel in the time series of images using the obtained geometric information, the corrected proton density values being indicative of changes in proton density due to changes in gas volume in the subject's lung;

produce a Fourier spectrum for each voxel in the field-of-view, each Fourier spectrum including a signal peak associated with a frequency of the subject's breathing rate, by Fourier transforming the corrected time series of images;

extract the signal peak in each voxel that is associated with a frequency of the subject's breathing rate from the produced Fourier spectra; and produce an image indicative of ventilation in the subject using the extracted signal peaks.

12. The MRI system as recited in claim 11 in which the computer system is programmed to produce the image indicative of ventilation by assigning a value of the extracted signal peaks to image intensity values in the image.

13. The MRI system as recited in claim 12 in which the computer system is programmed to produce a normalized image indicative of ventilation by normalizing image intensity values in each voxel in the image with respect to a total Fourier signal in the respective voxel.

14. The MRI system as recited in claim 13 in which the computer system is programmed to calculate the total signal as the sum of Fourier components at a voxel location of the respective voxel.

15. The MRI system as recited in claim 13 in which the computer system is programmed to produce an image indicative of a ventilation dependent blood volume using the image indicative of ventilation.

16. The MRI system as recited in claim 15 in which the computer system is programmed to produce the image indicative of ventilation dependent blood volume by:

i) forming from the time series of images, a temporal signal at each voxel in the field-of-view;

ii) producing a Fourier spectrum at each voxel by Fourier transforming the respective temporal signal;

iii) extracting a signal peak in each voxel that is associated with a frequency of the subject's breathing rate from the Fourier spectra produced in step ii);

iv) producing an image indicative of ventilation and ventilation dependent blood volume using the signal peaks extracted in step iii);

v) normalizing the image produced in step iv) with respect to a total Fourier signal for each respective voxel in the image; and vi) subtracting the normalized image indicative of ventilation and the image produced in step v).

17. The MRI system as recited in claim 11 in which the computer system is programmed to select the reference image to which image in the time series of images is registered as an image from the time series of images that represents the subject's lungs mid way between inhalation and exhalation.

* * * * *

UNITED STATES PATENT AND TRADEMARK OFFICE
CERTIFICATE OF CORRECTION

PATENT NO. : 8,660,634 B2
APPLICATION NO. : 13/453493
DATED : February 25, 2014
INVENTOR(S) : Samuel Patz et al.

Page 1 of 1

It is certified that error appears in the above-identified patent and that said Letters Patent is hereby corrected as shown below:

In the Specification

Column 1, Lines 8-10:
"This invention was made with government Support under Grant No. HL100606 awarded by the National Institutes of Health. The government has certain rights in this invention."

Should be:
--This invention was made with government support under HL096471, and HL100606 awarded by the National Institutes of Health. The government has certain rights in the invention.--.

Signed and Sealed this
Ninth Day of May, 2023

Katherine Kelly Vidal
*Director of the United States Patent and Trademark Office*